United States Patent [19]

Rahn

[11] Patent Number: 5,788,652
[45] Date of Patent: Aug. 4, 1998

[54] BLOOD SAMPLE COLLECTION DEVICE

[75] Inventor: Henry J. Rahn, Ridgewood, N.J.

[73] Assignee: S&H Diagnostics, Inc., Pittsburgh, Pa.

[21] Appl. No.: 823,424

[22] Filed: Mar. 24, 1997

[51] Int. Cl.⁶ .................. A61B 5/00; A61B 17/14
[52] U.S. Cl. .................. 600/577; 600/576; 606/182
[58] Field of Search .................. 606/181, 182, 606/167, 185; 600/576, 577

[56] References Cited

U.S. PATENT DOCUMENTS 4,653,513  3/1987  Dombrowski .
4,883,068  11/1989  Dechow ........................ 600/507
5,423,758  6/1995  Shaw ........................... 600/576
5,540,709  7/1996  Ramel .......................... 606/182

Primary Examiner—Glenn K. Dawson
Attorney, Agent, or Firm—Arthur M. Peslak

[57] ABSTRACT

A blood sample collection device is disclosed. The blood sample collection device includes an outer shell, a spring activated specialty needle for creating an incision in the patient where the blood sample is to be collected and a partially evacuated blood collection tube that is slidingly received in the blood sample collection device.

5 Claims, 2 Drawing Sheets

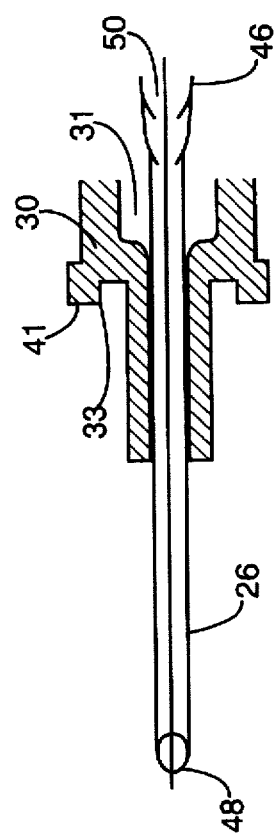

BLOOD SAMPLE COLLECTION DEVICE

BACKGROUND OF THE INVENTION

The present invention is directed to the field of disposable medical devices for collecting blood samples from a patient. These type of devices generally have a sharp implement for creating an incision into a human patient and also provision for collecting a blood sample from the incision. In particular, the device is used to collect blood from capillary bed sites near the skin layer of the patient.

The currently available devices for collecting blood suffer from one or more of the following defects: painful to the patient due to difficulty in controlling incision force and incision depth, susceptible to clogging from local tissue, long acquisition time, cumbersome for the operator to handle, and potential for the operator to accidentally prick himself or herself with the needle.

SUMMARY OF THE INVENTION

It is an objective of the present invention to overcome the problems associated with currently available blood collection devices. Accordingly, the present invention is directed to an improved device for collecting a blood sample from a human patient comprising an outer shell; an incision means for creating an incision in the patient and mounted in the outer shell wherein the incision is created by controlled longitudinal movement of the incision means in a compartment in the outer shell and a force provided by the incision means to create an incision is independent of any force applied by an operator to the patient; an activation means for activating the incision means in response to pressure being applied against the patient's skin wherein the activation means is mounted in the compartment in the outer shell, connected to the incision means and the compartment, and activates the incision means by longitudinal movement in the compartment in response to the pressure being applied against the patient's skin; and a collection means for collecting the blood sample from the patient wherein the collection means is slidingly received longitudinally in an open port in the outer shell and is fluidly connected to the incision in the patient created by the incision means after the incision means is activated by the activation means.

BRIEF DESCRIPTION OF THE DRAWINGS

FIG. 2 is a front cross-sectional view of a component of the present invention.

DETAILED DESCRIPTION OF THE INVENTION

Figure 1:
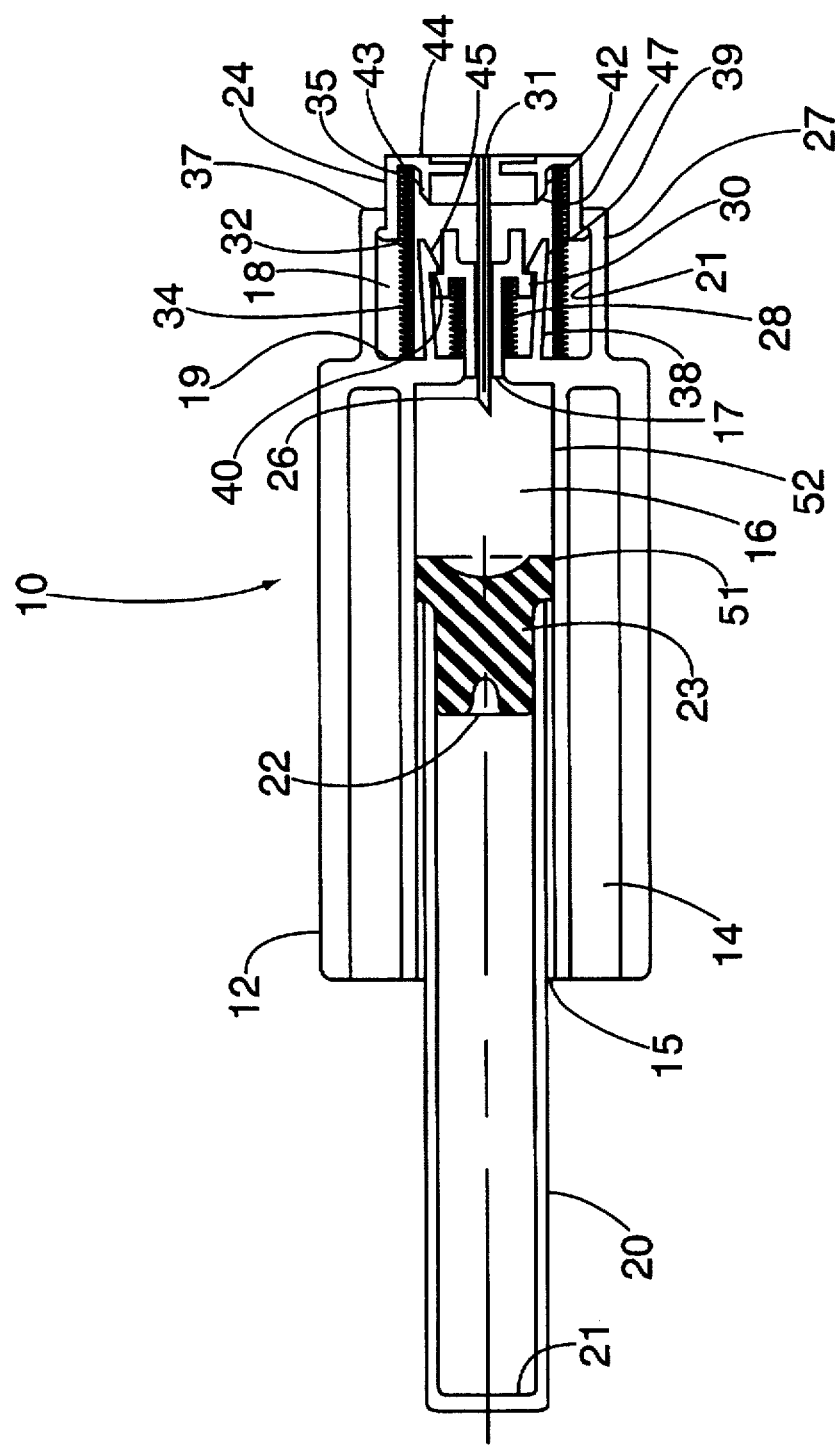
FIG. 1 is a front cross-sectional view of a blood sample collection device of the present invention.

The blood sample collection device 10 of the present invention is illustrated in FIG. 1. The blood sample collection device 10 comprises a molded partially hollow outer cylindrical shell 12. The partially hollow cylindrical shell 12 comprises longitudinally extending interior compartments 14, 16, and 18. Interior compartment 16 comprises a first open port 15 and is sized to slidingly receive a blood collection tube 20 through open port 15. Interior compartment 16 also comprises a second open port 17 axially aligned with first open port 15. Blood collection tube 20 is hollow with a closed end 21 and an open end 22. Open end 22 of blood collection tube 20 is fitted tightly with a rubber stopper 23.

Hollow compartment 18 contains a spring powered needle assembly 27. Spring powered needle assembly 27 comprises a needle 26. Needle 26 is slidingly received in second open port 17 as illustrated in FIG. 1. In the embodiment illustrated in FIG. 1, needle 26 is an SK-101 18 gauge stainless steel hypodermic needle. As shown in more detail in FIG. 2, needle 26 is provided with sharp edges 46 and 48 on its ends and a cannula 50 therebetween. Needle 26 is rigidly mounted in a hollow cylinder 30 as illustrated in FIG. 2. In use, the needle 26 and cylinder 30 will move together with no relative displacement between them. Needle 26 is attached to cylinder 30 by means of epoxy in the area designated 31 in FIG. 2. As shown in FIG. 1, needle 26 and cylinder 30 are loaded with a compression spring 28. The compression spring 28 is rigidly attached to the interior wall 19 of hollow compartment 18 on one end and to the front wall 33 of cylinder 30 on its opposite end.

The spring powered needle assembly 27 further comprises a second hollow cylinder 24. The second hollow cylinder 24 comprises an open port 31 on one end that is axially aligned with the needle 26 and sized to slidingly receive the needle 26. On the other end of hollow cylinder 24, a lip 32 is formed. The outer diameter of lip 32 is sized to be slidingly received on the interior wall 21 of hollow compartment 18. Hollow compartment 18 is also provided with a lip 33 which acts as a stop for second cylinder 24. Second cylinder 24 is also spring loaded with a second compression spring 34. Second compression spring 34 is rigidly attached to the interior wall 19 of hollow compartment 18 on its one end and the interior wall 35 of second cylinder 24 on the opposite end.

As shown in FIG. 1, hollow compartment 18 is provided with a first cylindrical cantilever projection 38. The first cylindrical cantilever projection 38 is provided on its free end with a triangular head 39. Triangular shaped head 39 is provided with a surface 40 that acts as a stop for needle 26 and cylinder 30. Surface 40 acts as a stop by engaging surface 41 on cylinder 30.

Second cylinder 24 is provided with a second cylindrical cantilever projection 42. The second cylindrical cantilever projection 42 is provided with a triangular head 43.

The method for using the blood collection device 10 will now be described. First, the blood acquisition site on the patient will be selected. The acquisition site should be prepared by massaging the area to stimulate surface blood flow. The acquisition site should then be wiped clean with cleaning alcohol and lydocaine to deaden the patient's nerve endings. The blood collection tube 20 will first be loaded through open port 15 and slid longitudinally into hollow compartment 16. The blood collection tube 20 is initially inserted into hollow compartment 16 only until the point where stop nibs 51 are contacted. The blood collection tube 20 is initially evacuated to a custom vacuum pressure with respect to the ambient pressure at the head of needle 26. In operation, the blood collection device 10 will be held by the operator on the end of the device 10 near to open port 15. The surface 44 on second hollow cylinder 24 on the opposite end of blood collection device 10 will be placed in contact with the patient's skin at the previously selected and prepared blood acquisition site. The blood collection device 10 is then pressed into the skin at the blood acquisition site. At that time, the spring powered needle assembly 27 is activated.

Due to the pressure applied by the operator against the patient' skin, the second cylinder 24 will begin to move longitudinally toward wall 19. Second compression spring 34 provides a resistive force against the longitudinal movement of the second cylinder 24 and controls the force needed to activate the spring powered needle assembly 27. As second cylinder 24 moves longitudinally into hollow cylinder 18 toward wall 19, a surface 47 on triangular head 43 will contact a surface 45 on triangular head 39. After contact, further longitudinal movement of second cylinder 24 will cause cylindrical cantilever projection 38 to move away from axis x—x. As cylindrical cantilever projection 38 moves away from axis x—x, needle 26 and cylinder 30 will no longer be held in place by surface 40. Thus, compression spring 28 will force needle 26 and cylinder 30 to move longitudinally toward the blood acquisition site on the patient.

When needle 26 contacts the blood acquisition site, sharp edge 46 will create an incision in the patient's skin. This action will result in capillary hemorrhage at the site where the incision is created. At this point, the operator will maintain pressure on the blood collection device 10 with one hand while pushing blood collection tube 20 longitudinally further into hollow compartment 16 until second stop 52 is reached. When second stop 52 is reached, the sharp edge 48 of needle 26 will puncture the rubber stopper 23 on the open end of blood collection tube 20. When the rubber stopper 23 is punctured by needle 26, the vacuum in blood collection tube 20 will cause blood to be drawn from the patient at the blood acquisition site through the cannula 50 in needle 26 and into the blood collection tube 20. The orifice size of cannula 50 in this embodiment is 0.090".

After the operator sees that enough blood has been collected, the blood collection tube 20 is longitudinally moved back to the first stop nibs 51. The blood collection device 10 is then removed from the blood acquisition site. At this point, pressure would be applied to the patient's wound at the blood collection site to promote clotting and a bandage would be place over the wound. The operator would then remove the blood collection tube 20 from the blood collection device 10.

The advantages of the blood collection device 10 of the present invention in comparison to existing blood collection devices are many. First, the force of the needle 26 when the incision is made is independent of the force used by the operator in pressing the blood collection device 10 against the patient's skin. Rather, the force of the needle 26 is always constant and determined by sizing of spring 28. In the embodiment just described, the force applied to the patient's skin by needle 26 is about 0.350 lb. Those of ordinary skill in the art will be able to select an appropriate spring 28 by considering such factors as needle diameter, needle travel etc. Through appropriate sizing of spring 28, the blood collection device 10 of the present invention can provide an incision with minimum discomfort for the patient. Second, the blood collection device 10 of the present invention is self-contained and simple for one individual to operate and safely collect a blood sample. By activating the needle 26 through pressure on the patient, the operator is protected from accidentally pricking himself or herself with the end of needle 26. Third, the penetration depth of the needle 26 into the patient's skin is precisely controlled. In the embodiment described herein, the penetration depth is about 3 mm. Fourth, the configuration of the needle 26 provides several advantages. Among the advantages are the ability to perform a precise incision that maximizes blood flow and minimizes invasiveness in the capillary beds, resistance of the port itself to clogging from local tissue, and creation of a flow path that increases blood aspiration and decreases blood acquisition time.

Those of ordinary skill in the art will recognize that the embodiment just described merely illustrates the principles of the present invention. Many modifications may be made thereto without departing from the spirit and scope of the invention as set forth in the following claims.

What is claimed is:

1. An improved device for collecting a blood sample from a human patient comprising:
   a) an outer shell;
   b) an incision means for creating an incision in the patient and mounted in the outer shell wherein the incision is created by controlled longitudinal movement of the incision means in a compartment in the outer shell and a force provided by the incision means to create an incision is independent of any force applied by an operator to the patient;
   c) an activation means for activating the incision means in response to pressure being applied against the patient's skin wherein the activation means is mounted in the compartment in the outer shell, connected to the incision means and the compartment, and activates the incision means by longitudinal movement in the compartment in response to the pressure being applied against the patient's skin; and
   d) a collection means for collecting the blood sample from the patient wherein the collection means is slidingly received longitudinally in an open port in the outer shell and is fluidly connected through the incision means to the incision in the patient created by the incision means after the incision means is activated by the activation means.

2. The device of claim 1 wherein the incision means comprises a longitudinally extending hypodermic needle with sharp edges on both ends and a cannula therebetween, a cylindrical shell in which the longitudinally extending hypodermic needle is rigidly mounted and a first compression spring rigidly attached to the cylindrical shell and the outer shell.

3. The device of claim 2 wherein the activation means comprises a cylinder with a surface for contacting the patient's skin and a second compression spring rigidly attached to the cylinder and the outer shell.

4. The device of claim 3 wherein the collection means is a tube initially at a lower pressure with respect to the ambient and adapted to be fluidly connected to the patient through the cannula in the longitudinally extending hypodermic needle.

5. An improved method for collecting a blood sample from a human patient comprising the following steps:
   a) selecting and preparing a blood acquisition site on the patient for acquiring the blood sample;
   b) placing a blood sample collection device in contact with the site;
   c) sliding a tube at a lower pressure than the ambient for collecting blood partially into an open port of the blood sample collection device;
   d) pressing the blood sample collection device onto the blood acquisition site and thereby activating an activation mean for activating a means for creating an incision in the patient;
   e) sliding the tube for collecting blood further into the blood sample collection device and into contact with the means for creating an incision in the patient;
   f) collecting the blood sample in the tube for collecting blood; and
   g) removing the tube for collecting blood from the blood sample collection device.

\* \* \* \* \*